US006790946B2

(12) United States Patent
Kwiatkowski et al.

(10) Patent No.: US 6,790,946 B2
(45) Date of Patent: *Sep. 14, 2004

(54) SYNTHESIS OF OLIGONUCLEOTIDES

(75) Inventors: Marek Kwiatkowski, Uppsala (SE); Ulf Landegren, Uppsala (SE); Mats Nilsson, Uppsala (SE)

(73) Assignee: Quiatech AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/952,944

(22) Filed: Sep. 12, 2001

(65) Prior Publication Data

US 2002/0051994 A1 May 2, 2002

Related U.S. Application Data

(63) Continuation of application No. 09/423,742, filed as application No. PCT/SE98/00893 on May 14, 1998, now Pat. No. 6,313,284.

(30) Foreign Application Priority Data

May 14, 1997 (SE) .............................. 9701783

(51) Int. Cl.[7] ....................... C07H 21/04; C07H 21/02; C12Q 1/68; C12M 1/36

(52) U.S. Cl. .................. 536/23.1; 536/24.2; 536/24.33; 536/25.3; 536/25.31; 536/25.33; 435/6; 435/174; 435/283.1; 435/287.2

(58) Field of Search ............................. 536/25.3, 24.2, 536/24.33, 25.31, 25.33, 23.1; 435/6, 174, 283.1, 287.2

(56) References Cited

U.S. PATENT DOCUMENTS

| 5,462,854 A | 10/1995 | Coassin et al. |
| 5,550,215 A | 8/1996 | Holmes |
| 5,552,540 A | 9/1996 | Haralambidis |
| 6,313,284 B1 * | 11/2001 | Kwiatkowski et al. ..... 536/25.3 |

FOREIGN PATENT DOCUMENTS

WO     WO 92/09615     6/1992

OTHER PUBLICATIONS

Alazzouzi et al., *Angew. Chem. Int. Ed. Engl.*, 1997, 36(13/14/):1506–1508.
Balgobin et al., *Chem. Scripta*, 1982, 20(4):198–200.
Bannwart et al. *Tetrahedron Letters*, 1989, 30(32):4219–4222.
Beaucage et al., *Tetrahedron*, 1992, 48(12):2223–2311.
Bellon et al., *Bioconjugate Chem.*, 1997, 8(2):204–212.
Chattopadhyaha et al., *Tetrahedron Letters*, 1979, 20(52):5059–5062.
Connolly et al., *Nucleic Acids Res.*, 1985, 13(12):4485–4502.
Fodor et al., *Science*, 1991, 251:767–773.
Griffin et al., *Tetrahedron Letters*, 1966, 7(34):4349–4354.
Hervé et al., *Nucleosides & Nucleotides*, 1991, 10:363–355.
Horn et al., *Nucleic Acids Res. Sym. Ser.*, 1985, 16:153–156.
Imai et al., *Bioconjugate Chem.*, 1990, 1(2):138–143.
Jäschke et al., *Tetrahedron Letters*, 1993, 34(2):301–304.

(List continued on next page.)

Primary Examiner—BJ Forman
(74) Attorney, Agent, or Firm—Fish & Richardson, P.C., P.A.

(57) ABSTRACT

A method of preparing an immobilized oligonucleotide having a free 3'-end comprises the steps of: i) preparing an oligonucleotide attached in a first position to a solid support via its 3'-end and having a free 5'-end; ii) binding said oligonucleotide in a second position remote from the 3'-end to the solid support; and iii) selectively releasing the 3'-end of the oligonucleotide from the solid support to obta the oligonucleotide attached to the support in said second position in a reversed orientation with a free 3'-end.

32 Claims, 10 Drawing Sheets

OTHER PUBLICATIONS

Kwiatkowski et al., *Nucleic Acids Res.*, 1996, 24(23):4632–4638.
Lehn et al., *Agnew. Chem. Int. Ed. Engl.*, 1990, 29(11):1304–1319.
Mikola et al., *Bioconjugate Chem.*, 1992, 3(2):182–186.
Nilsson et al., *Science*, 1994, 265:2085–2088.
Nitta et al., *FEBS Letters*, 1984, 166(1):194–198.
Pirrung et al., *J. Org. Chem.*, 1996, 61(6):2129–2136.
Rasmussen et al., *Anal. Biochem.*, 1991, 198(1):138–142.
Sekine et al., *Nucleic Acids Res. Sym. Ser.*, 1989, 21:33–34.
Southern et al., *Genomics*, 1992, 13(4):1008–1017.
Sund et al., *Nucleosides & Nucleotides*, 1988, 7(5–6):655–659.
Tanaka et al., *Nucleic Acids Res.*, 1986, 14(15):6256–6279.
Zeng et al., *J. Org. Chem.*, 1996, 61(26):9080–9081.

\* cited by examiner

SYNTHESIS OF OLIGONUCLEOTIDES

This application is a continuation (and claims the benefit of priority under 35 U.S.C. § 120) of U.S. application Ser. No. 09/423,742, filed Nov. 12, 1999, now U.S. Pat. No. 6,313,284 which is a 371 of PCT/SE98/00893 filed May 14, 1998. which claims priority to Swedish application 9701783-4 filed May 14, 1997. This application claims the benefit of priority of all prior applications. The disclosures of all prior applications are considered part of (and are incorporated by reference in) the disclosure of this application.

FIELD OF THE INVENTION

The present invention relates to oligonucleotide synthesis, and more particularly to in situ synthesis of oligonucleotides of inverse orientation.

BACKGROUND OF THE INVENTION

Oligonucleotide Arrays

Insights in the genetic make-up of man and other organisms increases rapidly. Moreover, information about the role of specific genes in diseases also accumulates at a rapid rate. Accordingly, there is a growing need for methods to analyse large sets of genetic factors in parallel. Oligonucleotide arrays, that is sets of oligonucleotides distributed in a two-dimensional pattern on the surface of a planar device, are promising as a means to study many nucleotide positions in a target DNA or RNA molecule. They can also be used to determine relative copy numbers or the presence of sequence variants of several different nucleic acid sequences in a sample. Numerous research groups have contributed to the development of methods for efficient construction of arrays, means to record the outcome of sample analyses, and for computation of the results.

Two principally distinct approaches have been taken for the construction of such oligonucleotide arrays. Individual oligonucleotides may be manufactured separately, purified, and characterized before they are immobilized in defined patches on a planar solid phase. Techniques used for this purpose include deposition via ink jet printing or direct transfer of liquid oligonucleotide samples with pen-like devices. These methods allow good control of the quality of the reagents immobilized, but arrays of high complexity, that is with more than around 1000 different specificities, are difficult to manufacture.

The other major approach to construct arrays is through in situ synthesis, where the stepwise synthesis of oligonucleotides is performed directly on the devices (1), (2). Typically, oligonucleotide synthesis proceeds from the 3'-end towards the 5'-end of the probe molecule. As detailed below, for some applications it would have been desirable if oligos were synthesized with a free 3'-end, but so far, stepwise synthesis in a 5'→3' direction is problematic. By applying methods developed for the construction of microprocessors, in situ synthesis of arrays of very high complexity has been achieved. The devices can be manufactured at limited cost and are already in use experimentally to investigate nucleic acid samples in order to distinguish and quantitate target sequences. Because the reagents are constructed in situ, it is not possible to ensure that individual oligonucleotides are of full length and without defects. With step-wise synthesis yields of considerably less than 100%, further compounded by the risk that oligonucleotides are damaged during synthesis by light or low pH, arrayed oligonucleotides are contaminated with truncated variants, significantly affecting analyses.

Specificity of Array-Based Analyses

Most commonly, oligonucleotides immobilized in arrays are employed to interrogate a nucleic acid sample on the basis of the differential hybridization stability of target molecules that are perfectly base-paired to an immobilized probe, versus ones that are mismatched in one or more nucleotide positions. This analysis can be enhanced by using very large sets of probe oligonucleotides that include many or most of the sequence variants that can be foreseen in a target sequence Moreover, the target sequence to be analysed can be mixed with equimolar amounts of a differentially labelled target sequence of known composition, to serve as an internal control in the analysis.

Besides DNA base-pairing, several molecular genetic assays also enlist the help of nucleic acid-specific enzymes for increased power of distinction among target sequence variants, or to identity rare target sequences in complex samples. Examples of such assays include ones taking advantage of the reduced efficiency of a primer, mismatched at its 3' end, to be extended by a DNA polymerase. This technique is used for DNA sequence variant distinction in methods variously referred to as allele-specific amplification, amplification refractory mutation screening, primed amplification of specific alleles, etc.

Polymerases can also be applied to distinguish target sequence variants by determining which nucleotide is incorporated at the 3' end of a primer, hybridizing just upstream of a variable nucleotide position, known as minisequencing or primer extension. Primer extension reactions have been used to analyze target sequences with single probes and with probes immobilized in arrays, as well as in situ (PRINS).

Both of the two classes of methods where polymerases are combined with hybridization probes require that immobilized probes have a free 3' end to be extended by the polymerase-assisted incorporation of nucleotides. They serve to efficiently distinguish among closely similar target sequence-variants. The enzyme-assisted extension also offers somewhat increased specificity of target recognition, since it is particularly important that the 3' end of the primer is correctly base-paired to the target sequence for the extension reaction to take place, adding to the specificity of target recognition in complex samples.

Another class of methods is based on the template-dependent joining of the 5' and the 3' end of probe molecules by a ligase. As with polymerases, this strategy places strict requirements on the basepairing of the two juxtaposed oligonucleotide ends to be joined, offering efficient distinction among related target sequence variants. The strategy also provides highly specific recognition of target sequences, even in complex DNA samples, by virtue of the requirement that two probe segments hybridize to the target sequence samples of techniques based on the use of ligases for sequence distinction include the oligonucleotide ligation assay, the ligase chain reaction, and padlock probes.

SUMMARY OF THE INVENTION

For reasons listed above, it would be very advantageous to work with arrays of the reversed, 5'→3' oligonucleotide orientation. As mentioned, synthesis of oligonucleotides of this orientation is difficult, and proceeds with substantially lower yield. This problem is even more serious for oligonucleotides to be synthesized in situ.

According to the present invention, the above problem is overcome by a method of preparing immobilized ologonucleotides having free 3'-ends, which method comprises the steps of:

(i) preparing an oligonucleotide attached in a first position to a solid support via its 3'-end and having a free 5'-end;

(ii) binding said oligonucleotide in a second position remote from the 3'-end to the solid support; and (iii) selectively releasing the 3'-end of the oligonucleotide from the solid support to obtain the oligonucleotide attached to the support in said second position in a reversed orientation with a free 3'-end.

In the following, the method of the invention will be described in more detail.

1) Synthesis of oligonucleotides in the usual 3' to 5' direction, anchoring the oligonucleotides to the solid phase via the 3'-hydroxyl and with the 5'-end projecting into solution;

2) reacting a group placed between the support and the 3'-end, or placed at a separate site on the support, with another reactive function present in the oligonucleotide or at its 5'-end, to form a structure in which oligonucleotides are bound to the support via at least two covalent bonds;

3) releasing the 3'-hydroxyl groups by breaking the oligonucleotides 3'-anchoring function;

4) final deprotection, yielding oligonucleotides bound to the solid-phase via a position other than the 3'-end.

Reversion of oligonucleotide orientation can be done in two principally different ways:

a) Performing the inversion process while the rest of the oligonucleotide is kept fully protected, and with the order of reactions as presented above; that is deprotection following release of the 3'-end.

b) Performing the inversion process only after oligonucleotide deprotection.

In both methods all truncated sequences are removed, however, in general only method (b) offers the possibility to simultaneously remove depurinated oligonucleotides. Exceptions from these rules will be presented in a further part of the text in conjunction with the listed examples.

The water-free chemistry required for inversions according to method (a) differs in some ways from the aqueous chemistry necessary in method (b), nevertheless, the structure of an oligonucleotide to be inversed can be presented dependent on localization of the function R, by one of the following two formulas:

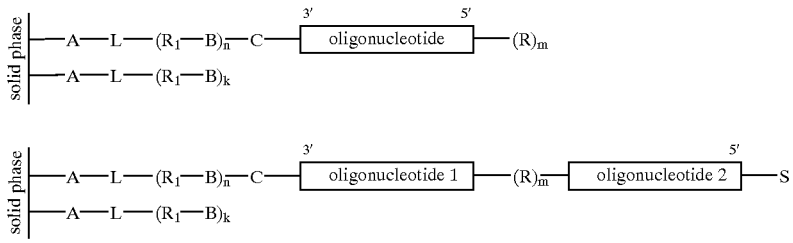

Figure 10:
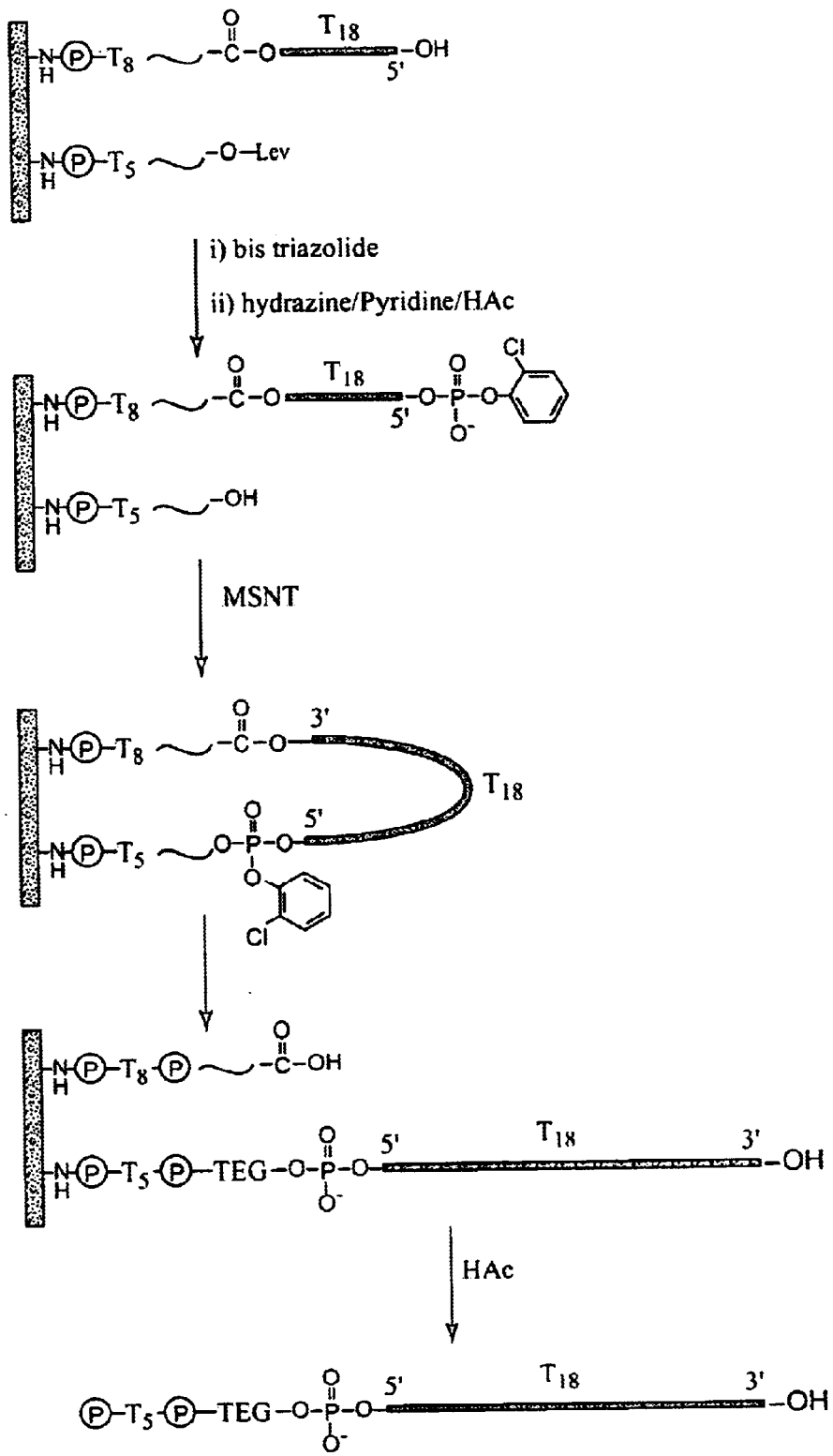

FIG. 10 is a schematic illustration of a reaction mechanism referred to in Example 4 below.

Figure 11:
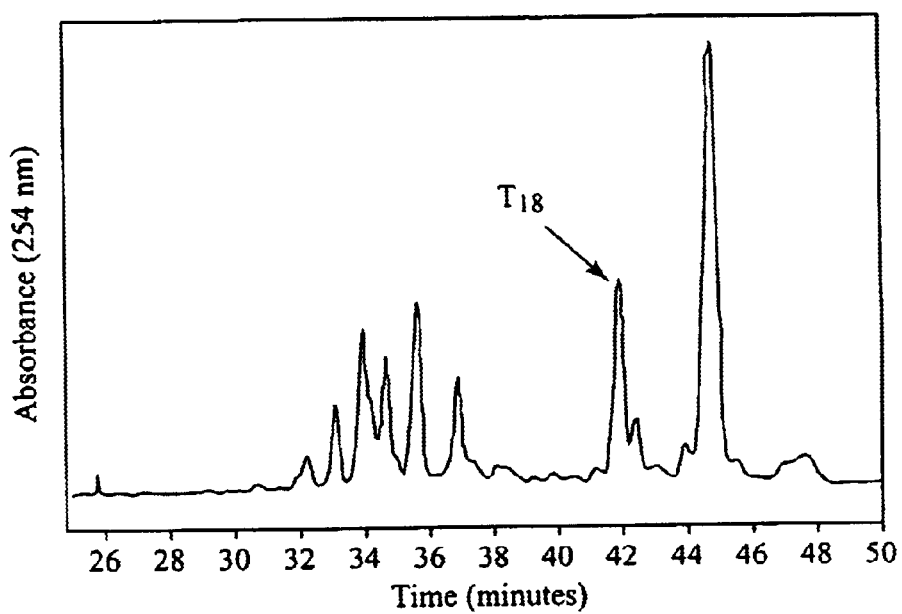

FIG. 11 is a diagram showing the result of capillary electrophoresis analysis of products of oligonucleotide inversion described in Example 4 below.

In the Figures, TEG is tetraethylene glycol residue, and DSi is disiloxyl residue.

DETAILED DESCRIPTION OF THE INVENTION

Figure 1:
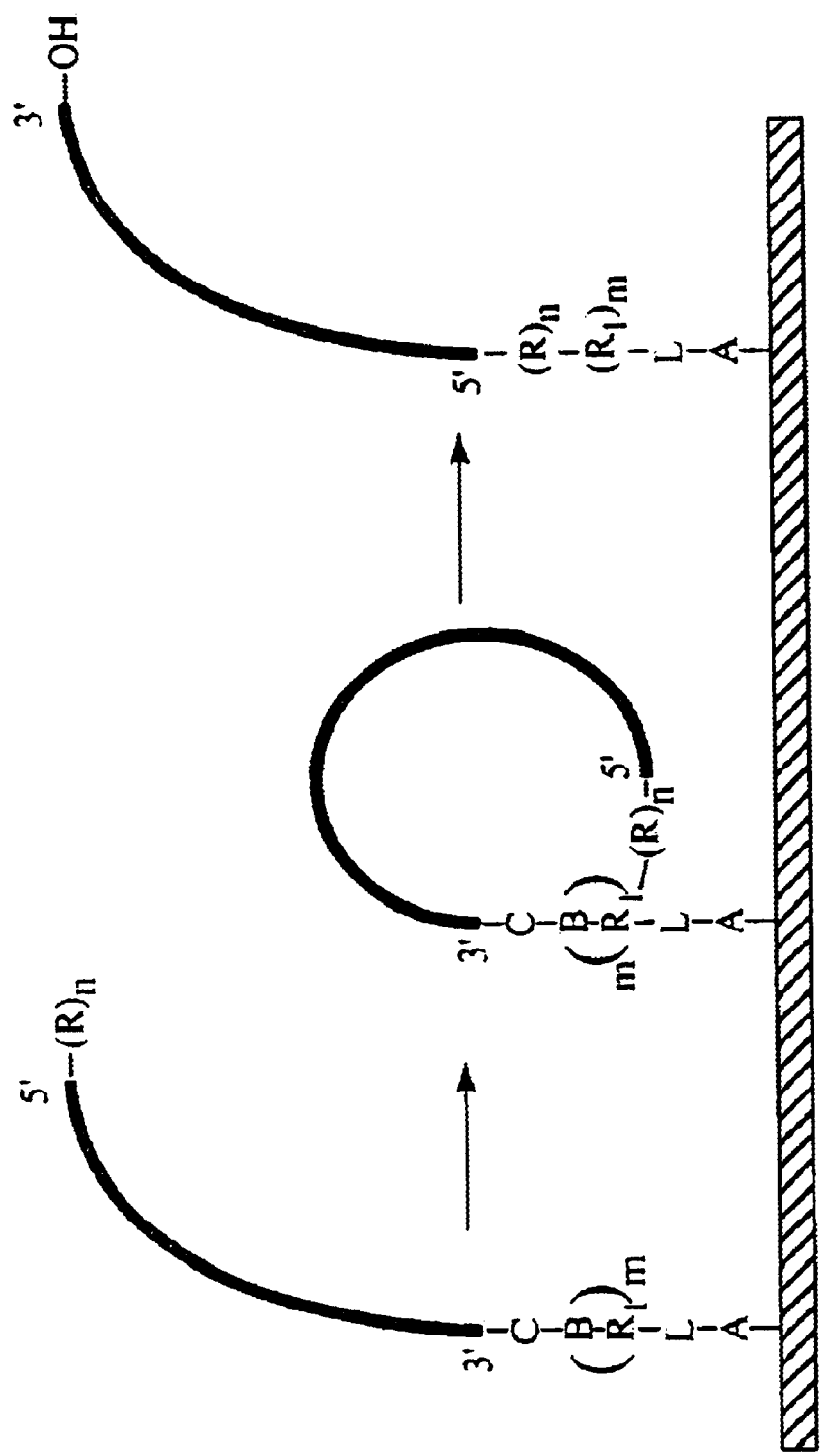
FIG. 1 is a schematic illustration of an embodiment of the method of the present invention which comprises reversing the orientation of an immobilized oligonucleotide through an intramolecular reaction.
Figure 2:
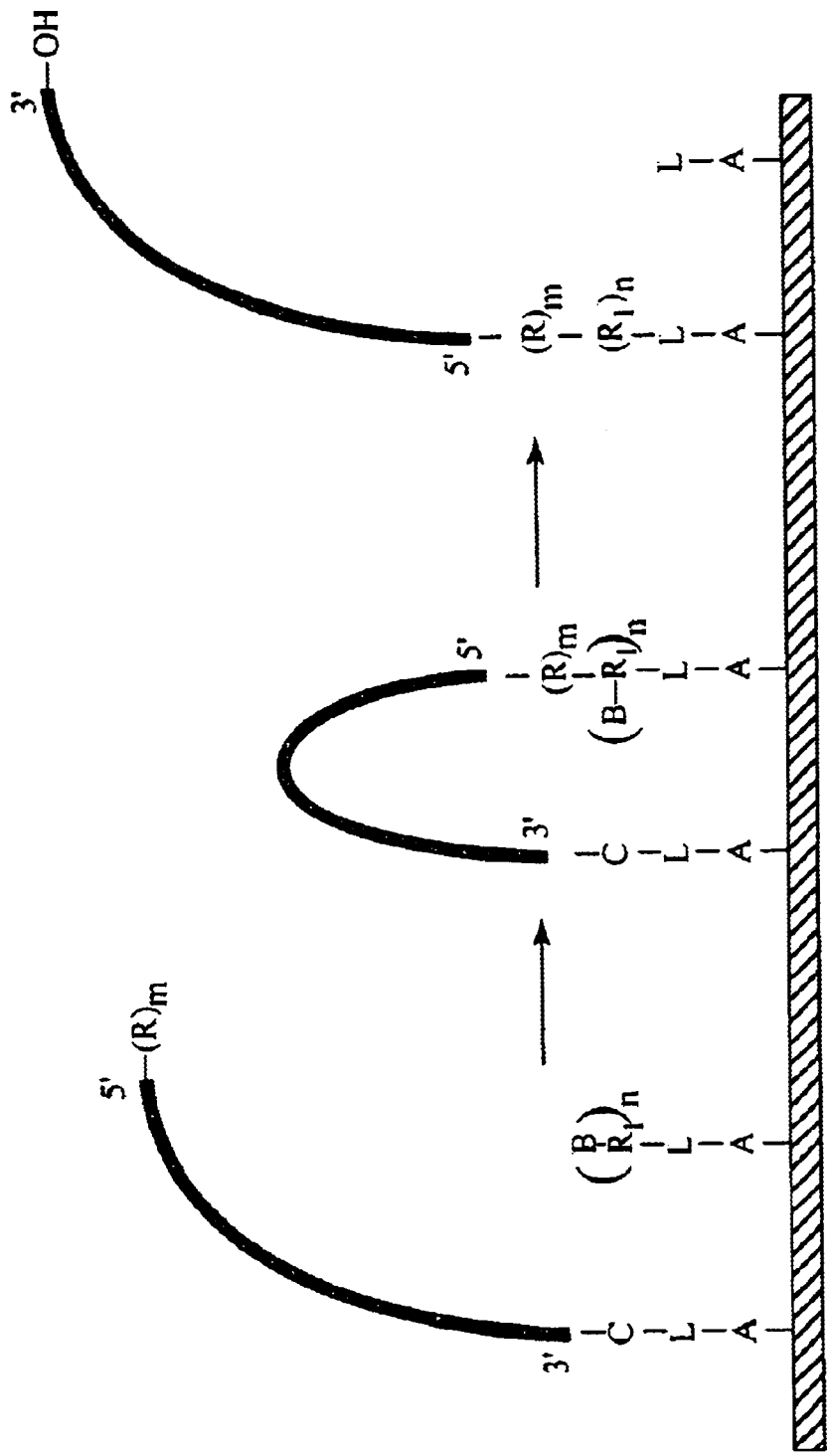
FIG. 2 is a schematic illustration of an embodiment of the method of the present invention which comprises reversing the orientation of an immobilized oligonucleotide through an intermolecular reaction.
Figure 3:
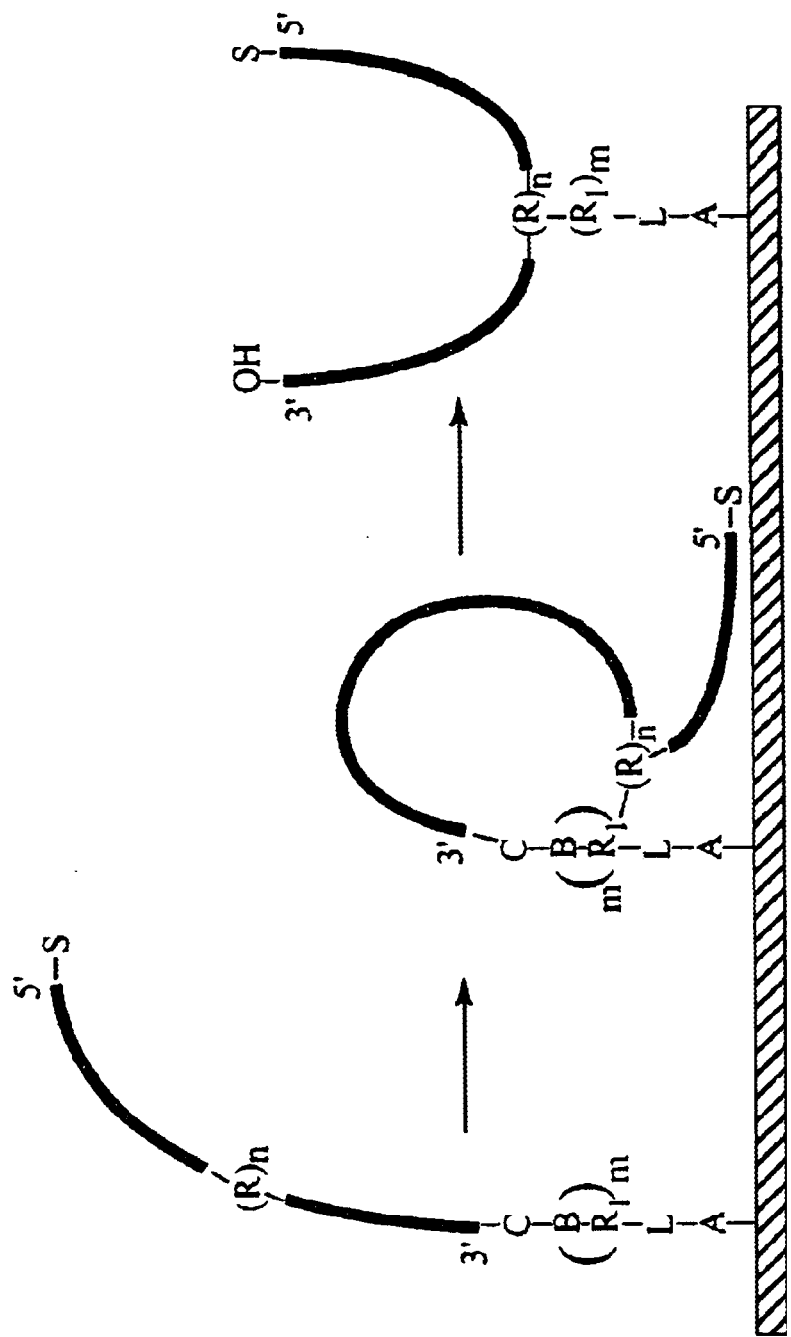
FIG. 3 is a schematic illustration of an embodiment of the method of the present invention which comprises reversing the orientation of an immobilized oligonucleotide to prepare an inverted product with free 3'- and 5'-ends.

The present invention thus provides a method for reversing the orientation of oligonucleotides synthesized in situ on a solid support. Method variants are schematically illustrated in FIGS. 1 to 3. An important characteristic of the method is that truncated sequences and shorter fragments resulting from acidic depurination can also be avoided in the final product. The method usually comprises the following steps:

All structural elements listed in these general formulas are linked via covalent bonds. Some of these bonds will be cleaved in the process of oligonucleotide inversion.

A wide range of non-porous as well as porous solid supports can be used in the methods according to the present invention. The group of preferred supports includes organic as well as inorganic materials and comprises polystyrenes, cross-linked polystyrenes, polypropylene, polyethylene, teflon, polysaccharides, cross-linked polysaccharides, silica, and various glasses. In certain cases supports are not fully compatible with some aspects of the chemistry used for oligonucleotide synthesis, their inversion or for deprotection. In particular, strong alkaline conditions at high temperature frequently used for deprotection of synthetic oligonucleotides or fluoride anion, as in tetrabutylammonium fluoride used for cleavage of silyl functions, cannot be applied on silica or glass supports as these reagents substantially degrade both of these supports.

The term oligonucleotide means a linear composition of ribo-, deoxyribonucleosides or modifications thereof, connected to each other by phosphodiester or phosphotriester bonds. Presenting the oligonucleotide 1 and oligonucleotide 2 in the lower formula above as two units, separated by a function(s) R, is simply a convenient way of describing the possibility of oligonucleotide reorientation with a new point of attachment that may be located other than at the 5'-end. If function(s) R is located at the 5'-end of the synthesized oligonucleotide, then there is no oligonucleotide 2.

Although, functions R and $R_1$ may denote a reactive function as such, they usually mean a unit linked to the rest of the molecule and containing a function necessary for interaction.

During the course, of oligonucleotide inversion, functions R and $R_1$ have to react with each other to form a covalent bond as illustrated in FIG. 1. Reactivity is therefore the main criterion describing their character, and in consequence, their relative position and chemical properties can be interchangeable. The probability for a particular reaction depends on reagent concentration. An intramolecular process of oligonucleotide inversion should therefore be more efficient, due to the higher local concentration of reagents, compared to a more common process of oligonucleotide immobilization. If desirable, the concentrations of both R and $R_1$ functions may be further increased by incorporating several of these functions in a row or in a branched form. Numbers k, m and n denote multiplicity of the above functions. m is within the interval from 1 to 20, and n and k are each within the interval from 0 to 20. Multiple reactive functions increase the probability of inversion.

Solid phase oligonucleotide synthesis usually produces material of high surface density. Oligonucleotide arrays characterized by such a high density of probes often show a seriously diminished tendency to interact with complementary sequences. It may therefore be advantageous to decrease this density in order to improve the final hybridization test. This can be done by limiting the number of reactive sites directly on the support, or by limiting the number of reactive sites on a linking function constructed on the support. The latter can be easily accomplished by coupling two different reagents added in a suitable proportion. In this case one of the above reagents will introduce a protected reactive group, thus preventing synthesis of an oligonucleotide at this particular site, while the ocher reagent will introduce the cleavable function C which does permit growth of an oligonucleotide (FIG. 2). This procedure provides not only the desired limitation of oligonucleotide density but it also results in a multiplicity of reactive sites useful for subsequent oligonucleotide inversion.

The required reactivity is often accomplished by using a pair of appropriate electrophile and nucleophile in place of R and $R_1$, although other less frequently used interactions e.g. photochemical reactions (3), electrochemical reactions, free radical reactions (4) or metal ion chelate formation (5) are also possible. Reactive functions R and $R_1$ do not have to be present on the synthesized oligonucleotide at all times. These functions can be activated just prior to oligonucleotide inversion by selective deprotection, by activation of appropriate unreactive functions with activating reagents (coupling reagents), or by derivatisation of a prefunctionalyzed oligonucleotide to form a pair of reactive functionalities.

The nucleophile among R or $R_1$ can be selected from the following functions:

1) A hydroxyl group—directly as in oligonucleotide 5'-hydroxyl or attached to the oligonucleotide 5'-end through a linker derived from a diol (6) or a polyol (7). Reagents are known that allow introduction and selective deprotection of a protected hydroxyl group (or their multiplicity) at any position of the synthetic oligonucleotide (8).

2) An amine group can be situated at the 5'-end of an oligonucleotide using conventional chemistry. Also reagents for 5'-end attachment of a linker arm terminating in an amine are commercially available. If an acid labile protecting group is used for protection of the amino group, then synthesis of a fully deprotected oligonucleotide, with a Protected amine group is possible. As for the hydroxyl group, a long range of reagents are known that can be used for introduction of an amine group at a preselected position within the oligonucleotide (9), (8).

3) A thiol group can be introduced at the 5'-position of an oligonucleotide using known reagents (10), however, deprotection requires strong electrophiles or reducing agents (usually an excess of another thiol) that interacts with functions necessary for the intended oligonucleotide inversion. To avoid these problems, a new type of reagents was developed, indicated by numeral 1 in FIG. 4, in which a thiol function is protected by an acid labile protecting group (Kwiatkowski—unpublished results). The mild acidic conditions applied for the deprotection of the thiol group do not influence most thiol-reactive functions.

4) Hydrazine, hydrazide, semicarbazides, carbohydrazides and hydroxylamine functions can be used as powerful nucleophiles (11). Reagents introducing these functions into an oligonucleotide can easily be prepared starting from described compounds (12). If necessary, an acyl function, usually used for the protection of the hydroxylamine, hydrazine or hydrazide groups, can be easily substituted by an acid labile function, as it was done with the chemically similar amine group above.

The frequently used nucleophiles mentioned above and any other, easily recognised to those who are skilled in the art, can form stable bonds after reacting with selected electrophiles.

The most preferred function to react with an amine function is a carboxyl group activated in situ by a suitable carbodiimide or another coupling reagent (13). Other means of carboxyl group activation is the formation of mixed anhydrides or active esters. In a similar process a phosphomonoester can be activated by a carbodiimide to form an active imidazole-derivative that undergoes reaction with the amine present in the system (14). Yet another preferred amine-reactive function, capable to react with an amine group, is an aldehyde group. This function can be introduced by several means as it can be exemplified by periodate oxidation of a cis-diol system (often a ribonucleotide component attached to deoxyribo-oligonucleotide), or by reacting a NHS-ester of 4-carboxy benzaldehyde with an appropriately situated amino function. Aldehyde function reacts with a reactive amino group to form unstable imine, subsequently stabilized by a reducing agent to form a stable secondary amine (15). The carbonyl group present in an aldehyde is also a reagent of choice for reaction with hydrazine or hydroxylamine function. Reactions of these functions with aldehydes produce, contrary to amines, relatively stable hydrazones and oxazones which can be even further stabilized by their reduction.

The thiol reactive group may be an activated disulfide, a maleimide, or an active halogen. The active halogens are typically α-haloacyls. Useful halogens include fluorine, chlorine, bromine and iodine, with iodine and bromine being preferred. Reagents useful for this invention can be obtained commercially (16).

A most preferred function for reaction with a hydroxyl group is a phosphodiester, a H-phosphonate or a phosphomonoester. A phosphodiester function can be easily introduced at the 5'-end by means of several phosphorylating reagents like 2-chlorophenylphosphoro-bistriazolide, etc. Attachment of a phosphodiester function to the 3'-end of an oligonucleotide can be done by a standard phosphoroamidite coupling followed by basic elimination of an alkene (usually acrylonitrile) in order to convert a phosphotriester function to a phosphodiester. The selective conversion of a particular phosphotriester to a phosphodiester in the presence of other phosphotriesters is also possible if said phosphate is protected using groups removable in other than basic conditions. Examples are photolabile functions (17) and functions removable by metal (palladium) catalysis (18). In the even simpler alternative, all oligonucleotide phosphotriester bonds, with the exception of the phosphotriester to be converted to the phosphodiester are prepared as a non base-labile methyl derivative (19).

Water-free conditions and a suitable activating reagent are a prerequisite for reaction of phosphodiester or phosphomonoester group with a hydroxyl. Several efficient activating reagents (coupling reagents) are known to those who are skilled in art (20), the most preferred ones being mesitylenesulfonyl nitrotriazole (MSNT) and dicyclohexylcarbodiimide (DCC).

The successful coupling of an oligonucleotide hydroxyl group to a phosphodiester function results in the formation of a new phosphotriester bond. However, usual phosphodiesters present in an oligonucleotide chain are lacking the possibility of selective hydrolysis after reaction with an oligonucleotide hydroxyl group and conversion to phosphodiesters. This results in a random cleavage with formation of three different phosphodiesters. To avoid this problem it is necessary to introduce a function B which is preferentially cleavable. Such groups are known and most of them belong to the category of substituted aryl esters or functions cleavable in a base-catalyzed β-elimination process (21). It is also possible to envisage functionalities removable by reduction (22) or in a photochemical process. The most suitable groups to be used as B are substituted forms of: 2-chlorophenyl, 2,4-dichlorophenyl, 2-nitrophenyl, 4-nitrophenyl, 4-nitrophenylethyl and 2-cyanoethyl.

Function C plays a central role in the present strategy. In a methodology for oligonucleotide inversion performed after oligonucleotide deprotection, function C is designed to withstand all the steps of synthesis and the basic conditions used for oligonucleotide deprotection, yet being susceptible to selective cleavage after inversion under conditions that are not harmful for the rest of the molecule It is of primary importance in the present strategy that cleavage of a function C results in the liberation of a free 3'-hydroxyl group. In view of advantages offered by oligonucleotide inversion regarding purity of the final material, it would also be beneficial to use even other types of functions C, leading to formation of functionalities other than 3'-hydroxyl groups. A tetrasubstituted disyloxyl group, removable by fluoride anions, has been presented as a group fulfilling these criteria (23). Other preferred functions are disubstituted siloxyl removable by fluoride anion (24), photolabile groups exemplified by substituted 2-nitrophenyl benzyl ethers (25), groups removable under redox conditions exemplified by substituted benzyl ethers (26) or functions removable by metal-ion catalysis (27). One additional possibility for a group applicable as a C-component is a substituted cis-diol system, exemplified by a specially designed ribonucleotide unit. In this approach, one of the cis-diol hydroxyls is linked to the 3'-end of an oligonucleotide via a phosphodiester or phosphotriester bond and the other hydroxyl is substituted by any of the above listed hydrolytically stable functions. The final removal of the above function will result in disruption of the phosphodiester bond to generate a free 3'-hydroxyl group.

All of these cleavable functions can also be used in a methodology for inversion of fully protected oligonucleotides. However, here the demands on the cleavable unction are not so strict, since the formation of the new bond between oligonucleotide and a solid phase precede deprotection and cleavage of the linkage. In consequence, a standard ester linkage, cleavable in aqueous ammonia, can be used as function C. An example of a reagent suitable for introduction of an ester function inside an oligonucleotide chain is shown at 2 on FIG. 4.

If the discussed function R is not located at an oligonucleotide 5'-end, but rather inside its chain, for instance in the middle of its length, then the inverted product will have both 3'- and 5'-ends free. Such a localized oligonucleotide can be used as a circularizable, ligation-based probe (padlock probe) (28) if its 5'-end is substituted with a phosphate group.

Therefore, function S present at the 5'-end of the oligonucleotide (FIG. 3) represents a phosphate, a protected phosphate, or any other oligonucleotide 5'-hydroxyl protecting group. Contrary to the oligonucleotide inversion presented in FIG. 1, the process leading to formation of immobilized padlock probes (FIG. 3) does not remove all truncated sequences. However, with proper protection of the 5'-end by group S, it is possible to selectively remove all shorter, and therefore unprotected fragments by enzymatic digestion (29).

Group A has the role of anchoring the rest of the molecule to the solid support.

Group L is a linker, connecting the support with rest of the oligonucleotide.

The only requirement on both groups is to be chemically resistant to conditions applied during oligonucleotide synthesis, inversion and deprotection. Chemical resistance means chat all the above components are stable with respect to the chain breakage. The most preferred group A is an amide, a phosphodiester, a phosphotriester or an ether. The linking function L may comprise from none to several elements linked together. These elements may be constituted of nucleotides, but other non-nucleotidic elements are also allowed. An example of a non-nucleotidic element used for construction of linker L is a properly protected diol-phosphoramidite, like oligoethylene glycols (6). Yet another possible function of linker L is a multiplication of starting points for oligonucleotide synthesis. This will, in consequence, result in increased density of a final inverted product. To achieve it, a reagent generating a dendrimeric structure is applicable. Several of such a compounds are known, and preferred reagents for this purpose are branching, disubstituted phosphoramidites (7).

The following Examples further illustrate the invention and are not to be construed as limiting of the specification and claims in any way.

EXAMPLE 1

Inversion of a Fully-Protected, Model Oligonucleotide in a Non-Aqueous System a) Synthesis of Phosphoramidite 2 (FIG. 4) to be Used as an Equivalent of $R_1$-B Unit A suspension of sodium borohydride (1.25 g, 32 mmol) in dry THF was added during a period of 10 min to a solution of 3-chloro-4-hydroxyphenylacetic acid (3.0 g, 15.9 mmol) in dry THF (50 ml). The mixture was stirred for additional 15 min and a solution of trimethylsilyl chloride (6.9 g, 63.6 mmol) in THF (30 ml) was added dropwise during a period of 30 min. The mixture was stirred for 3 hr, quenched with water (20 ml), acidified with conc. HCl, partitioned between chloroform and water and extracted with chloroform (3×150 ml). The combined extracts were evaporated in vacuo and dried by coevaporation with toluene. TLC analysis showed presence of an essentially pure compound (2.55 g, 92%) having the expected NMR (CDCl$_3$) characteristics. This crude material (1.40 g, 8.1 mmol) was coevaporated with dry pyridine (20 ml), dissolved in pyridine (50 ml) and dimethoxytritylchloride (3.1 g, 9.0 mmol) was added. Stirring was continued at room temperature for 5 hr. The mixture was partitioned between saturated aqueous sodium hydrogen carbonate and chloroform, extracted with chloroform (3×100 ml) and the organic extracts were evaporated. The partially protected 1-dimethoxytrityloxy-2-(3-chloro-4-hydroxyphenyl)ethane was isolated after flush chromatography on Silica gel 60 (Merck) and using 2% ethanol in chloroform for the elution. Combined fractions containing the pure product (2.85 g, 74%) were evaporated and coevaporated with toluene.

The above material (2.39 g, 5.0 mmol) was dissolved in anhydrous dichlormethane (30 ml) and dry triethylamine (1.52 g, 2.10 ml, 15 mmol), followed by 2-cyanoethyl-N,N-diisopropylaminophosphochloridate (1.78 g, 7.55 mmol) were added. After 15 min stirring at room temperature, the reaction mixture was quickly partitioned between saturated aqueous sodium hydrogen carbonate and dichlormethane and extracted with dichlormethane (2×50 ml). The residue obtained after evaporation of the organic phase was dried by coevaporation with toluene and purified on a short silica gel column, prepared and eluted with hexane dichlormethane-:triethylamine 45:45:10. Fractions containing the desired product 2 (FIG. 4) were combined, evaporated and coevaporated with dry acetonitrile to yield an oil (2.75 g, 84%) having the expected $^{31}$P-NMR characteristics and purity.

b) Solid-Phase Assembly of a Functionalized Oligonucleotide

A spherical (50–70 µm) polystyrene support, derivatized with aminomethyl groups (ABI, 22 mmol/g, 10 mg, 0.2 µmol) was placed in a cassette and subjected to two consecutive couplings of compound 2 (FIG. 4) on a Gene Assembler Plus (Pharmacia Biotech AB). The coupling time was increased to 6 min, followed by a prolonged capping time (3 min) and standard iodine oxidation. Under these conditions a coupling yield of over 98% was regularly achieved. The support was treated on the machine by triethylamine:acetonitrile 1:1 for 1 hr to convert phosphoramide diester and phosphotriester bonds to the phosphoramide monoester and phosphodiester, respectively. Next, a coupling of reagent 3 (FIG. 4) was performed to introduce a fluoride anion-labile disyloxyl linkage and a starting thymidine unit (FIG. 5). This was followed by the addition of 14 thymidines to form a pentadecathymidylic acid (T$_{15}$), and removal of the 5'-end trityl group.

c) Secondary Attachment of the Oligonucleotide to the Solid-Phase

Figure 6:
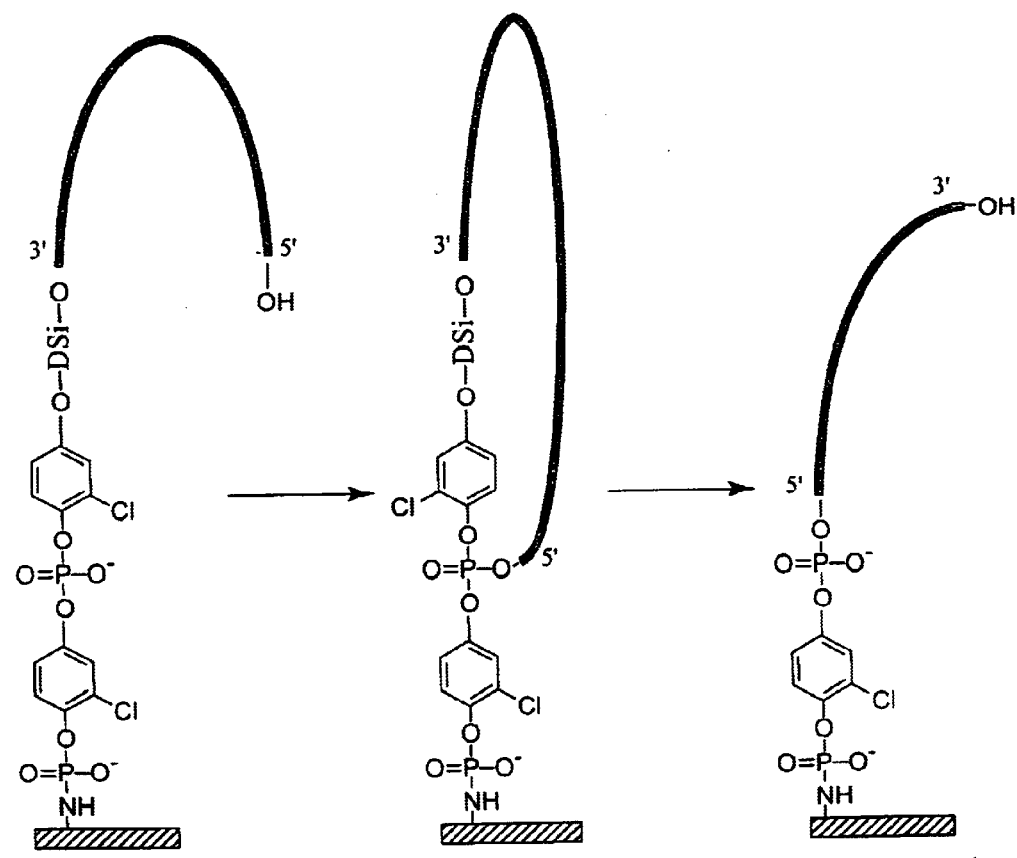
FIG. 6 is a schematic illustration of the intramolecular inversion procedure described in Example 1 below.

The cassette was opened, the derivatized support was transferred to an Eppendorf tube and washed with dry pyridine. MSNT (1.5 mg, 10 µmol) in pyridine (200 µl) was added. The reaction proceeded at room temperature for 3 hr with occasional shaking. After centrifugation, the liquid phase was removed and the support was washed with acetonitrile (3×1.0 ml).

d) Oligonucleotide Deprotection and Release of the Free 3'-hydroxyl (FIG. 6)

The washed support was treated with tetrabutylammonium fluoride (TBAF) (0.5 M, 200 µl) for 2 hr at room temperature. Although TBAF is sufficient to cleave the disiloxyl bridge, 2-chlorophenyl ester bond and 2-cyanoethyl phosphotriester bonds, the support was further treated with conc. aqueous ammonia to resemble standard oligonucleotide deprotection conditions. Additionally, a treatment with 4-nitrobenzaloxime and tetramethylguanidine may be introduced prior to fluoride treatment to reverse possible side-reactions caused by MSNT. The mixed liquid phase after fluoride/ammonia treatment was isolated and the solid support was washed with water (3×0.5 ml). The combined extracts were evaporated, desalted on a NAP 10 column (Pharmacia Biotech AB) and analyzed on a HPLC system (Hitachi Merck La Chrom), using a LiChrospher RP 18 (5 mm) (Merck) and linear gradient of solvent A: acetonitrile 5% v/v in triethylammonium acetate 0.1 M (pH 7) and solvent B: acetonitrile 40% v/v in triethylammonium acetate 0.1 M (pH 7). This analysis revealed the presence of cleaved, non-inverted oligonucleotides accompanied by a side-product—5'-sulfonylated oligonucleotide and several shorter DNA fragments. unsuitable for inversion.

e) Release of the Inverted Oligonucleotide from the Solid Support

The remaining support was treated with 50% aqueous acetic acid at room temperature for 3 hr to cleave the acid labile phosphoramide bond that links the inverted oligonucleotide to the support. The isolated liquid phase was evaporated and analyzed on a HPLC as above, confirming that approximately 50% of the oligonucleotide underwent inversion. Moreover, as expected, no traces of shorter products, or 5'-sulphonylated material was found.

EXAMPLE 2

Figure 7:
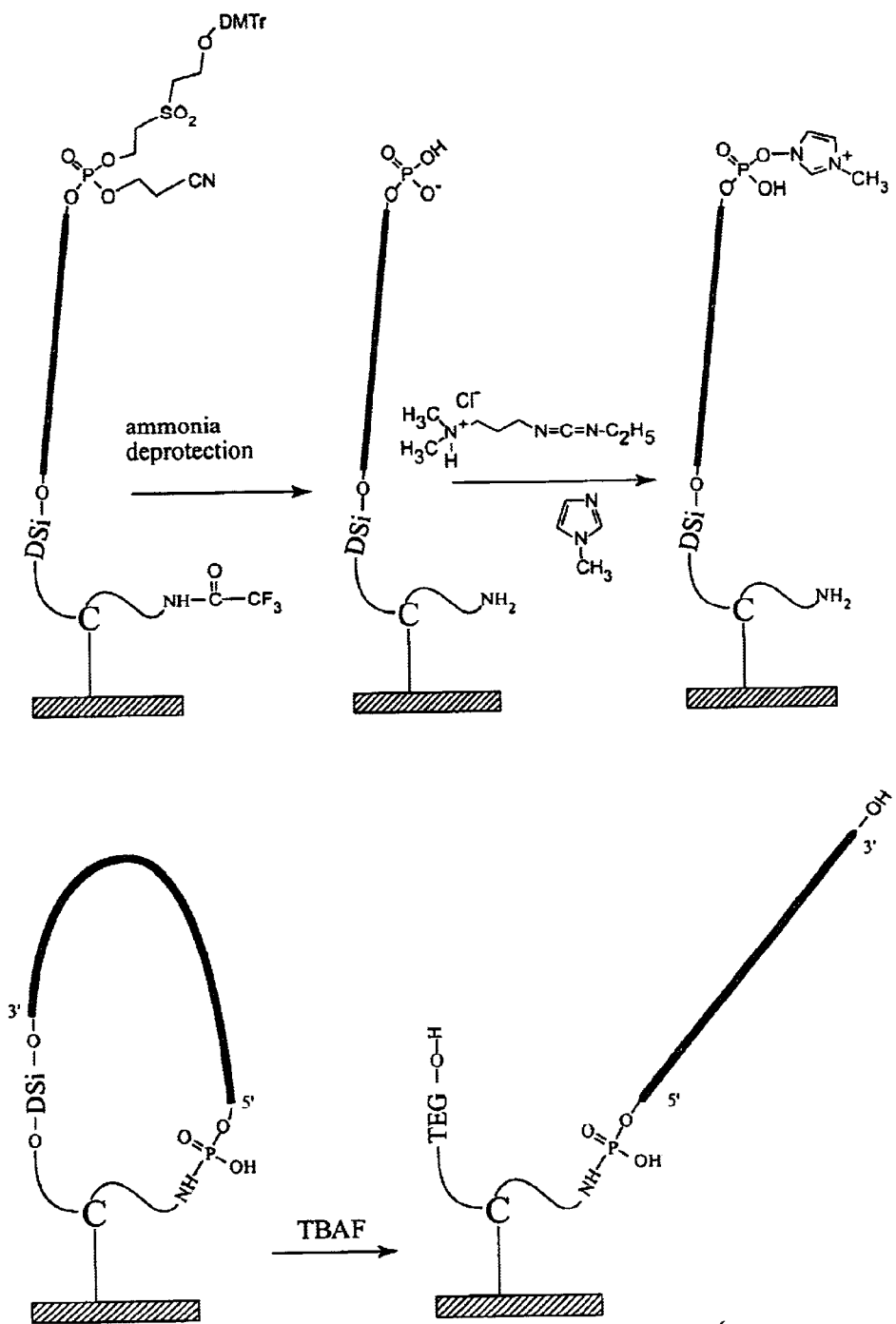
FIG. 7 is a schematic illustration of the intramolecular inversion procedure described in Example 2 below.

Inversion of a Deprotected Model Oligonucleotide in an Aqueous System Based an the Formation of a Phosphoramide Bond (FIG. 7)

A polystyrene support, derivatized with a hydroxyl group (23), was subjected to three consecutive couplings of N-4 amine-modified dC phosphoramidite 4 (FIG. 4) (9). These couplings were followed by single coupling of reagent 3 (FIG. 4) and 14 couplings of T amidite to form a model oligonucleotide T$_{15}$. Finally, a phosphate was introduced at the 5'-end of the oligonucleotide. The support was treated with conc. aqueous ammonia at 60° C. for 2 hr and washed extensively with water. The inversion process was started by addition of 1-ethyl-3-(3-dimethylaminopropyl)-carbodiimide (EDAC) (0.2 M, 100 µl) to the support suspended in N-methyl imidazole buffer (0.2 M. 200 µl). The mixture was incubated with occasional shaking at 50° C. for 5 hr, washed extensively with water (3×1.0 ml), ethanol (1.0 ml) and dried by washing with acetonitrile (2×1.0 ml). TBAF (0.5 M, 200 µl) was added to the support and the suspension was kept at room temperature for 2 hr. Finally, the support was washed with water (3×1.0 ml) and ethanol (2×1.0 ml).

EXAMPLE 3

Figure 8:
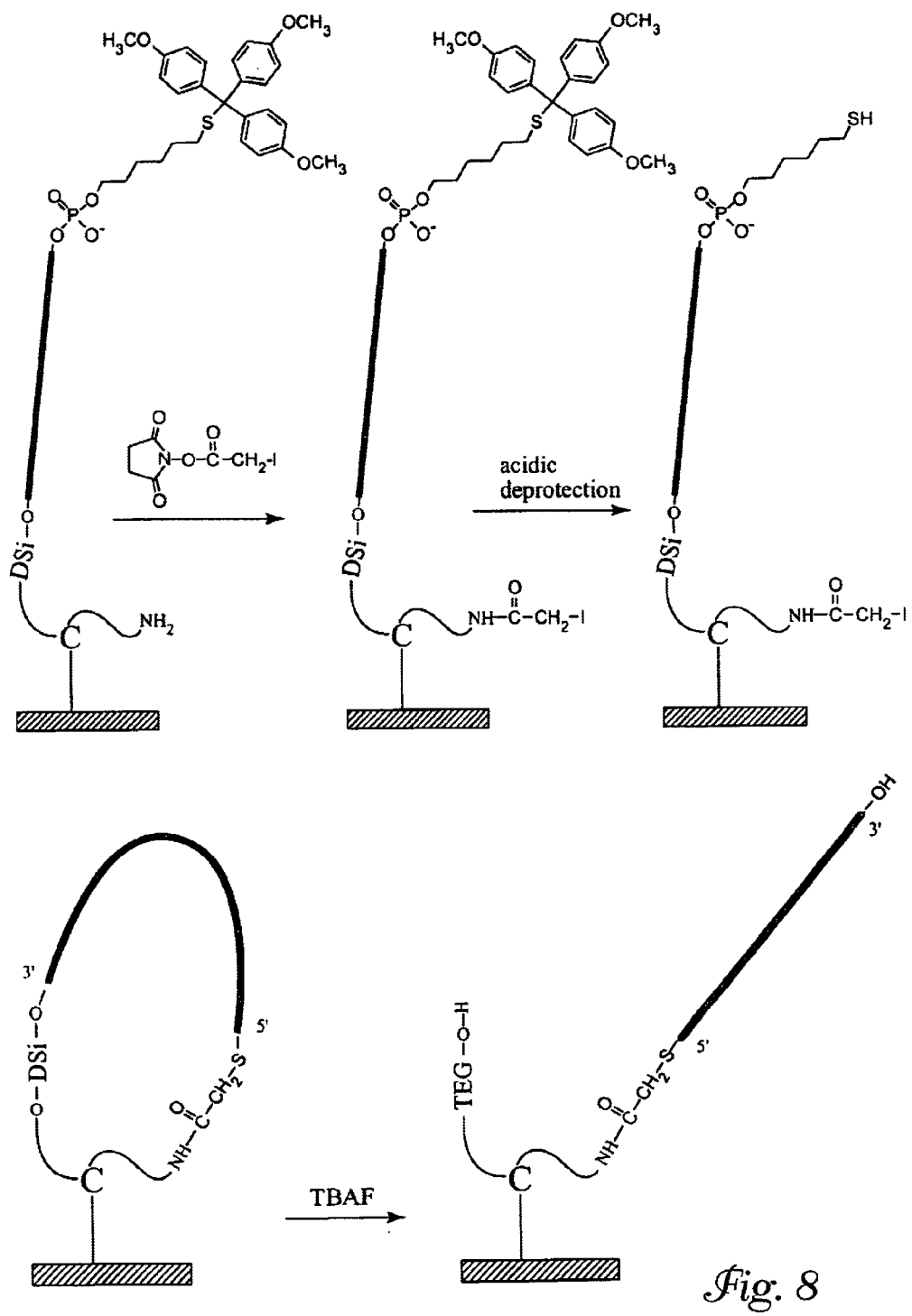
FIG. 8 is a schematic illustration of the intramolecular inversion procedure described in Example 3 below.

Inversion of a Deprotected Model Oligonucleotide in an Aqueous System, Based on the Formation of a Thioether Bond (FIGS. 8)

a) Synthesis of a New Reagent for Incorporation of a Thiol Function into an Oligonucleotide 4-Chlorohexanol (2.73 g, 20 mmol) was added to the magnetically stirred solution of potassium thiobenzoate (3.70 g, 20 mmol) in dimethylformamide (30 ml) and the mixture was stirred at room temperature for 1 hr. DMF was evaporated in vacuo by coevaporation with n-butanol (2×20 ml), and the residue was suspended in ethanol (50 ml). Sodium hydroxide (2.0 M, 15 ml, 30 mmol) was added and the hydrolysis of the thioester was followed by TLC (Kieselgel 60 $F_{254}$), using 10% ethanol in chloroform as an eluent. After 20 min the mixture was acidified with hydrochloric acid (3.0 M, 10 ml, 30 mmol) and trimethoxytrityl chloride (3.69 g, 10 mmol) was added in one portion. To this stirred bright-yellow solution, triethylamine was introduced in small portions until the yellow mixture became distinctly pale. The mixture was partitioned between saturated aqueous sodium hydrogen carbonate and dichlormethane, extracted with dichlormethane (3×100 ml) and the organic phase was evaporated and dried by coevaporation with toluene (100 ml). The residue was flash chromatographed on silica gel to obtain 4-TMTr-S-hexanol (4.15 g, 89%). This material was reacted with 2-cyanoethyl-N,N-diisopropylaminophosphochloridate as described in Example 1 to yield after flash chromatography phosphoroamidite 1 (FIG. 4) as a colourless oil (yield=86%).

b) Oligonucleotide Assembly and its Inversion.

Figure 4:
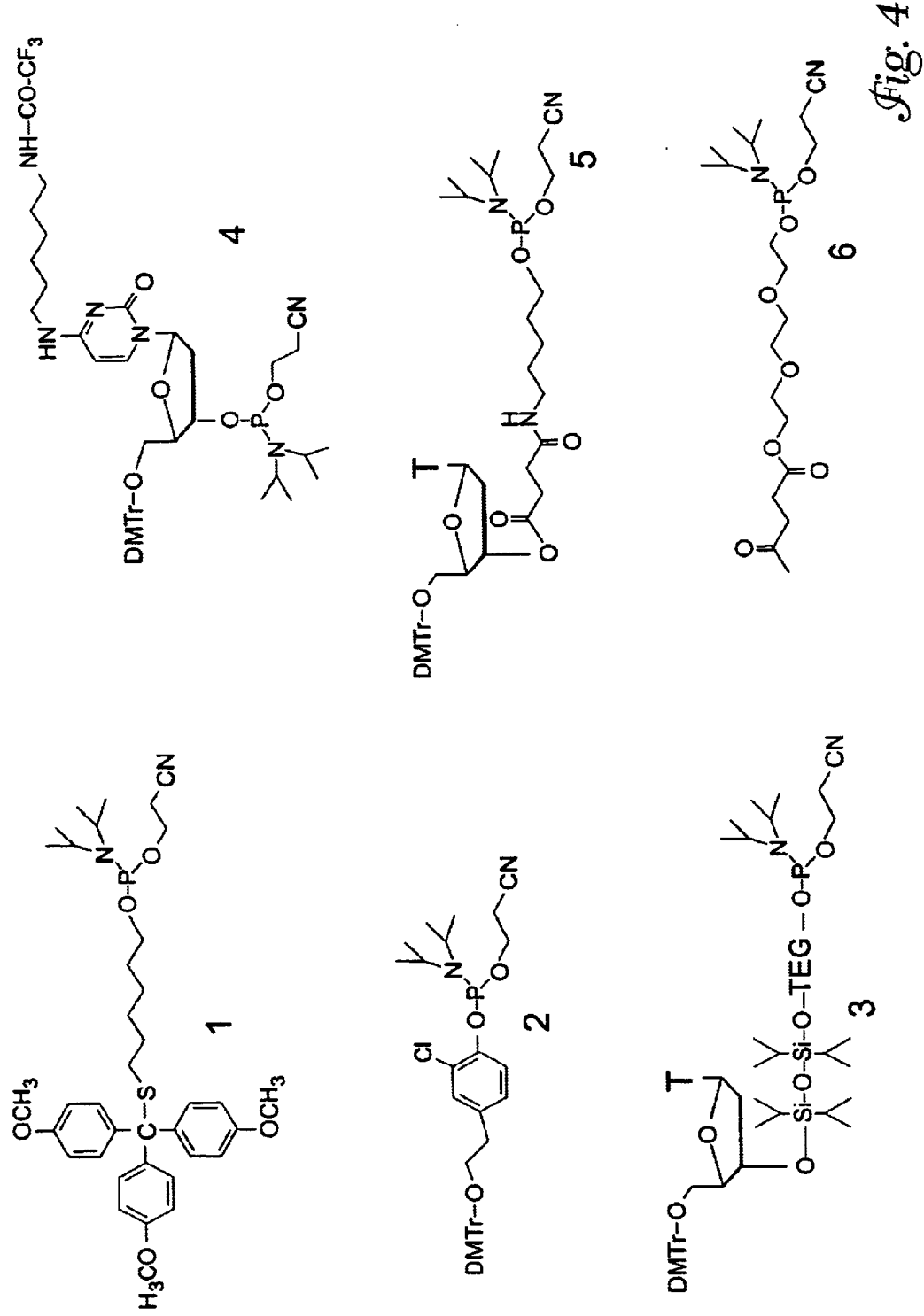
FIG. 4 is an illustration of the structures of six compounds referred to in the following description.
Figure 5:
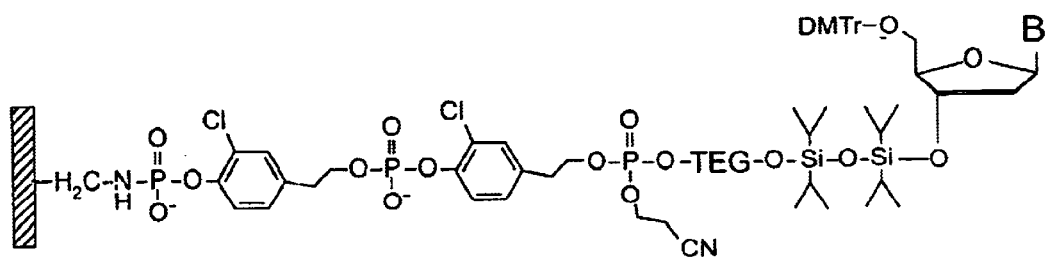
FIG. 5 is an illustration of a solid-phase derivatized for oligonucleotide synthesis described in Example 1 below.

A polystyrene bound model oligonucleotide $T_{15}$ was constructed exactly as described in Example 2, with the exceptions that only a single coupling of amino-modified dC 4 (FIG. 4) was done, and coupling of the 5'-phosphate group in the former example was substituted by a single coupling of compound 1 (FIG. 4). Due to the presence of a reactive sulphur atom, the standard iodine oxidation of P(III) to P(V) was substituted by tert-butylhydrogen peroxide (9.1 M) in dichloromethane for 10 min. The usual aqueous ammonia deprotection and washings were performed with an unopened cassette. The support was treated for 1 hr at room temperature with N-hydroxysuccinimide ester of iodoacetic acid (10 mg) dissolved in DMF (200 μl) and mixed with a hepes buffer (0.2 M, pH 7.4, 200 μl) to acylate the reactive amino group. The cassette was washed with water, then with ethanol, and subjected to a detritylation on the synthesis instrument for 1 min. The support was transferred to an Eppendorf tube, suspended in hepes buffer (0.2 M. pH 7.4, 1.0 ml), degassed with argon and incubated at room temperature for 12 hr. Finally, She support was washed with water, dried by washing with acetonitrile, and treated with TBAF as described earlier. No attempts were made to quench residual thiol or iodoacetamido groups.

EXAMPLE 4

Figure 9:
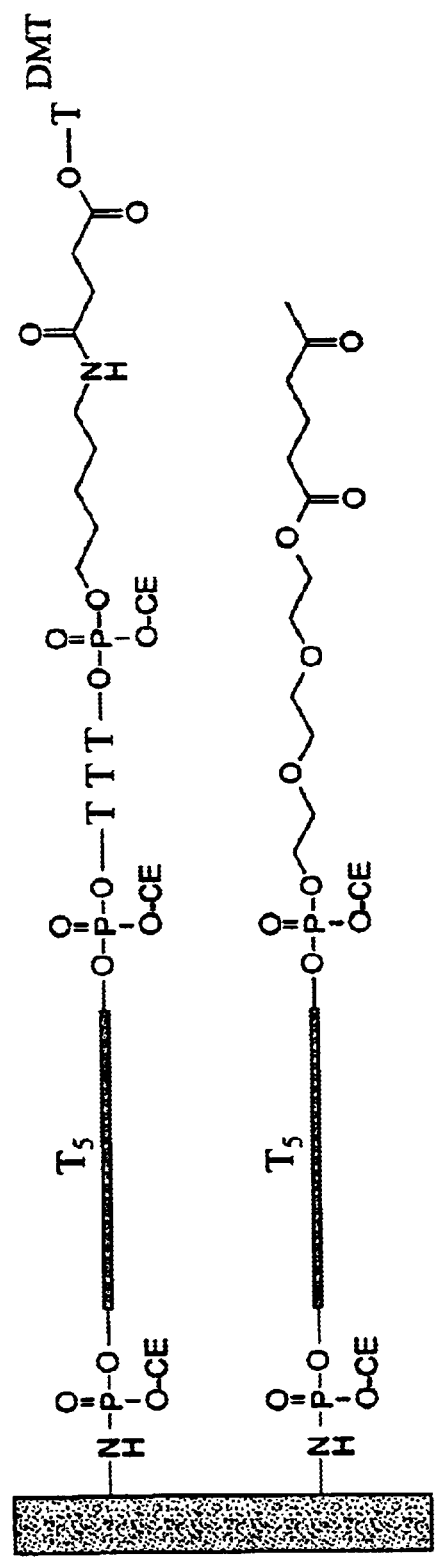
FIG. 9 is an illustration of a solid phase derivatized for oligonucleotide synthesis as described in Example 4 below.

Decreased Surface Density of Inverted Oligonucleotides; Application of Capillary Electrophoresis in the Study of a Model System Cassettes charged with aminomethyl polystyrene (ABI) were placed in the oligonucleotide synthesizer and subjected to five consecutive couplings of T amidite. Mixtures of T amidite and levulinyl protected amidite 6 (FIG. 4) were prepared in different proportions (1:2, 1:4 and 1:8) and used for coupling to the appropriate support. Partially capped supports were reacted twice with T amidite followed by coupling of cleavable amidite 5 (FIG. 4). Solid-phases, derivatized in this manner (FIG. 9), were finally used in a synthesis of a model octadecathymidylic acid ($T_{18}$). The 5'-O-DMTr protecting groups were removed and solid-phase bound oligonucleotides were phosphorylated using a 0.1 M o-chlorophenylphosphorobistriazolide (30) solution in pyridine:acetonitrile 1:1 for 10 min. Further, supports were washed with acetonitrile and subjected to a mixture of 0.1 M hydrazine in pyridine acetic acid 4:1 for 10 min to remove the levulinyl function (FIG. 10). Solid-phases were transferred to separate Eppendorf tubes, washed with dry pyridine (2×1 ml), and treated with 0.1 M MSNT in pyridine for 2 hr with occasional shaking. Following this condensation, supports were washed with acetonitrile (3×1 ml), and treated with a mixture of syn-4-nitrophenylbenzaloxim and tetramethylguanidine in dioxane:water 1:1 for 16 hr to accomplish a proper hydrolysis of o-chlorophenyl-phosphotriester bond and reversal of some possible modifications of nucleotide bases that may be caused by MSNT. Reaction mixtures were transferred to larger screw cap tight flasks and incubated at 60° C. for 16 hr after addition or concentrated aqueous ammonia (4 ml). Mixtures were transferred to round-bottom flasks and all volatile matters were evaporated in vacuum. The residues were subjected to treatment with 80% aqueous acetic acid for 120 min to achieve the final cleavage of inverted material from the support. Finally, mixtures were evaporated, coevaporated twice with water (2 ml), and analyzed by capillary electrophoresis, demonstrating the presence of substantial amounts of material longer than the non-inverted $T_{18}$ (FIG. 11). This result strongly supports the conclusion that the reaction followed the mechanism presented in FIG. 10.

EXAMPLE 5

Primer Extension Assay for Probing the Presence of a Free 3'-Hydroxyl Group

A 21-mer oligodeoxynucleotide was synthesized at a 0.2 μmol scale and inverted as described in the Example 4 but without releasing it from the support. Fifteen bases located at the 3'-end were complementary to a synthetic oligonucleotide template (M13–30comp). The M13–30 comp sequence is 5'-GTCGACCTGCAGGCATGCAAGCTTGGCACT-3' (seq. ID. No. 1). The particles were suspended in a mixture of water and ethanol 1:1, and 10 μl portions were withdrawn and placed in separate tubes. The analyzed material was washed 3× using PBS buffer containing 50 mg BSA/ml. A typical 20 μl extension reaction contained polystyrene beads with oligonucleotide, 1 pmol M13–30comp, 1× Klenow fill-in buffer, BSA 50 μg/ml. 100 mM each dATP, dGTP, TTP, 2.5 μM dCTP, radioactive α32p dCTP (2 μl) (3000 Ci/mmol; DuPont), 5U Klenow polymerase. In parallel, two reactions containing all listed components but lacking template oligonucleotide or DNA polymerase, respectively, were also prepared. The reactions were incubated at RT for 15 minutes and terminated by the addition of 1 μl 0.5M EDTA. The beads were washed with (4×1 ml) PBS buffer with addition of 0.1% of Tween 20. To remove the hybridized template which could also serve as a primer and incorporate label the beads were washed twice with 1 ml of denaturing solution containing 1M NaCl, 0.1M NaOH and 0.1% Triton X-100 and 1×1 ml with 1M NaCl, 0.1M Tris-HCl pH 7.5 and 0.1% Triton X-100.

Supports were placed in a Beckman scintillation counter and the incorporated radioactivity was recorded as follows.
a) Reaction without template—385 cpm
b) Reaction without polymerase—35 cpm
c) Solid-phase primer extension on the inverted oligonucleotide—146250 cpm
d) Solid-phase after denaturing washes—76370 cpm It is therefore evident that substantial amounts of inversion had occurred, yielding material with free and enzymatically active 3'-ends.

References:
(The entire disclosures of the references are incorprated by reference herein.)
1. Southern E M, Maskos U, Elder K J. Analyzing and comparing nucleic acid sequences by hybridization to 1. arrays of oligonucleotides: Evaluation using experimental models. *Genomics* 1992; 13:1008–1017.
2. Fodor S P, Read J L, Pirrung M C, Stryer L, Lu A T, Solas D. Light-directed, spatially addressable parallel chemical synthesis. *Science* 1991; 251(4995):767–73.
3. Imai N, Kometani T. Crocker P J, et al. Photoaffinity heterobifunctiqnal cross-linking reagents based on N-(azidobenzoyl)tyrosines. *Bioconjugace Chem.* 1990; 1(2):138–43.
4. Zeng Q, Rokita S E. Tandem quinone methide generation for cross-linking DNA. *J. Org. Chem.* 1996; 61(26):9080–9081.
5. Lehn J-M. Perspectives in supramolecular chemistry— From molecular recognition towards molecular information processing and self-organization. *Angew, Chem. Inc. Ed.* 1990; 29:1304–1319.
6. Jaschke A, Fürste J P, Cech D, Erdmann V A. Automated incorporation of polyethylene glycol into synthetic oligonucleotides. *Tetrahedron Lett.* 1993; 34(2):301–304.
7. Bazin H, Roget A, Teoule R. Phosphoramidite reagents for the easy preparation of polylabelled oligonucleotide probes. *Nucleosidos & Nucleocides* 1991; 10:363–366.
8. Clontech—Product Catalogue. 1996.
9. Sund C, Ylikoski J, Hurskainen P, Kwiatkowski M. Construction of europium ($Eu^{+3}$) labelled oligo DNA hybridization probes. *Nucleosides & Nucleocides* 1988; 7(5–6):655–659.
10. Connolly B A, Rider P. Chemical synthesis of oligonucleotides containing a free sulphydryl group and subsequent attachment of thiol specific probes. *Nucleic Acids Res.* 1985; 13(12):4485–502.
11. Nitta N, Kuge O, Yui S, Tsugawa A. Negishi K, Hayatsu H. A new reaction useful for chemical cross-linking between nucleic acids and proteins. *Febs. Lett.* 1984; 166 (1):194–8.
12. Mikola H, Hanninen E. Introduction of aliphatic amino and hydroxy groups to keto steroids using O-substituted hydroxylamines. *Bioconjug. Chem.* 1992; 3(2):182–6.
13. Bodanszky M. *Principles of peptide synthesis*. Springer-verlag, 1993.
14. Rasmussen S R, Larsen M R, Rasmussen S E. Covalent immobilization of DNA onto polystyrene microwells: the molecules are only bound at the 5' end. *Anal. Biochem,.* 1991; 198(1):138–42.
15. Bellon L, Workman C T. Jervis T C, Wincott F E. Post-synthetically ligated ribozymes; An alternative approach to iterative solid-phase synthesis. *Bioconjugate Chem.* 1997; 8(2):204–212.
16. Haugland R P. *Handbook of fluorescent probes and research chemicals*. Molecular Probes, 1996.
17. Pirrung M C, Fallon L, Lever D C, Shuey S W. inverse phoshotriester DNA synthesis using photochemically-removable dimethoxybenzoin phosphate protecting group. *J. Org. Chem.* 1996; 61(6):2129–2136.
18. Bannwarth W, Küng E. Bis(allyloxy)(diisopropylamio)-phosphine as a new phosphinylation reagent for the phosphorylation of hydroxy functions. *Tetrahedron Lett.* 1989; 30(32):4219–4222.
19. Alazzouzi E, Escaja N, Grandas A, Pedroso E. A straightforward solid-phase synthesis of cyclic oligodeoxyribonucleotides. *Angew. Chem. Int. Ed. Engl.* 1997; 36 (13/14): 1506–1508,
20. Christodoulu C. Oligonucleotide synthesis. In: Agrawal S, ed. *Protocols for Oligonucleotides and Analogs*. Totowa: Humana Press, 1993.
21. Beaucage S L, Iyer R P. Advances in the synthesis of oligonucleotides by the phosphoramidite approach. *Tetrahedron* 1992; 48(12):2223–2311.
22. Balgobin N, Kwiatkowski M, Chattopadhyaya. A novel strategy for the chemical synthesis of DNA and RNA fragments using 2-oxymethyleneanthraquinone (MAQ) as a terminal phosphate protecting group. *Chem. Scripta* 1982; 20:198–200.
23. Kwiatkowski M, Nilsson M, Landegren U. Synthesis of full-length oligonucleotides: cleavage of apurinic molecules on a novel support. *Nucleic Acids Res.* 1996; 24(23):4632–4638.
24. Holmberg L. Method and means for oligonucleotide synthesis. Published PCT application WO 92/09615, 1992.
25. Tanaka T, Tamatsukuri S, Ikehara M. Solid phase synthesis of oligoribonucleotides using o-nitrobenzyl protection of 2'-hydroxyl via a phosphite triester approach. *Nucleic Acids Res.* 1986; 14(15):6265–79.
26. Griffin B E, Reese C B. Stephenson G F, Trentham D R. Oligoribonucleotide synthesis from nucleoside 2'-benzyl ethers. *Tetrahedron Lett.* 1966; 7:4349–4354.
27. Sekine M, Nakanishi T. Oligoribonucleotide synthesis by use of the ((2, (methylthio)phenyl)thio)methyl (MPTM) group. *Nucleic Acids Res. Symp. Ser.* 1989, 21:33–34.
28. Nilsson M, Malmgren H, Samiotaki M, Kwiatkowski M, Chowdhary B P, Landegren U. Padlock probes: circularizing oligonucleotides for localized DNA detection. *Science* 1994; 265(5181):2085–8.
29. Morn T, Urdea M S. Enzymatic purification of chemically synthesized oligodeoxyribonucleotides prior to removal from a solid-support. *Nucleic Acids Res. Sym. Ser.* 1985(16):153–156.
30. Chattopadhyaya J, Reese C. *Tetrahedron Lett.* 1979; 20:5059.

What is claimed is:

1. A method of preparing an immobilized oligonucleotide having a free 3'-end, which method comprises the steps of:
   (i) preparing an oligonucleotide attached in a first position to a solid support via its 3'-end and having a free 5'-end;
   (ii) binding said oligonucleotide in a second position remote from the 3'-end to the solid support; and
   (iii) selectively releasing the 3'-end of the oligonucleotide from the solid support to obtain the oligonucleotide attached to the support in said second position in a reversed orientation with a free 3'-end.

2. The method according to claim 1, wherein the binding of the oligonucleotide to the support in step (ii) comprises coupling said second position of the oligonucleotide to a position between the 3'-end of the oligonucleotide and the support in an intramolecular reaction.

3. The method according to claim 1, wherein the binding of the oligonucleotide to the support in step (ii) comprises coupling said second position of the oligonucleotide to a separate function on the solid support in an intermolecular reaction.

4. The method according to claim 1, wherein step (ii) comprises binding the oligonucleotide to the solid support via the 5'-end of the oligonucleotide.

5. The method according to claim 1, wherein step (ii) comprises binding the oligonucleotide to the solid support via an intermediate part of the oligonucleotide.

6. The method according to claims 1, wherein the oligonucleotide prepared in step (i) comprises a first reactive function at its 5'-end, or between the 3'- and 5'-ends of the oligonucleotide, and a second reactive function between the 3'-end of the oligonucleotide and the solid support, and wherein step (ii) comprises reacting said first and second reactive functions with each other.

7. The method according to claims 1, wherein the oligonucleotide prepared in step (i) comprises a first reactive function at its 5'-end, or between the 3'- and 5'-ends of the oligonucleotide, and a second reactive function between the 3'-end of the oligonucleotide and the solid support, and wherein step (ii) comprises reacting two adjacent oligonucleotides with each other such that said first reactive function of one oligonucleotide reacts with said second reactive function of the other oligonucleotide.

8. The method according to claims 1, wherein the oligonucleotide prepared in step (i) comprises a first reactive function at its 5'-end, or between the 3'- and 5'-ends of the oligonucleotide, wherein a second reactive function is provided on the solid support, and wherein step (ii) comprises reacting said first and second reactive functions with each other.

9. The method according to claims 6, wherein said first and second reactive functions are reacted with each other through a reaction selected from nucleophilic-electrophilic, photochemical, free-radical, and metal ion chelate formation reactions.

10. The method according to claims 1, wherein steps (ii) and (iii) are performed with the oligonucleotide fully protected.

11. The method according to claims 1, wherein the oligonucleotide prepared in step (i) is deprotected prior to performing steps (ii) and (iii).

12. The method according to claims 1, wherein the immobilized oligonucleotide prepared in step (i) comprises a structure of the general formula:

$$A\text{-}(L)_p\text{-}(R_1)_n\text{-}C\text{-}OLIGONUCLEOTIDE\text{-}(R)_M$$

wherein:
A is a support-anchoring group,
L is a linker,
$R_1$ and R are reactive functions capable of reacting with each other to form a stable bond, or groups that can be selectively converted to such reactive functions,
C is a selectively cleavable group,
m is an integer from 1 to 20,
n is an integer from 0 to 20, and
p is 0 or 1.

13. The method according to claims 11, wherein the immobilized oligonucleotide prepared in step (i) comprises a structure of the general formula:

$$A\text{-}(L)_p\text{-}(R_1)_n\text{-}C\text{-}OLIGONUCLEOTIDE\ 1\text{-}(R)_M\text{-}OLIGONUCLEOTIDE\ 2\text{-}S$$

wherein:
A is a support-anchoring group,
L is a linker,
$R_1$ and R are reactive functions capable of reacting with each other to form a stable bond, or groups that can be selectively converted to such reactive functions,
C is a selectively cleavable group,
m is an integer from 1 or 20,
n is an integer from 0 or 20, and
p is 0 or 1,
and S is a phosphate, protected phosphate or 5'-hydroxyl protecting group.

14. The method according to claim 12, wherein the solid support exhibits a structure of the general formula:

$$A\text{-}(L)_p\text{-}(R1)_n$$

wherein:
A is a support-anchoring group,
L is a linker,
$R_1$ and R are reactive functions capable of reacting with each other to form a stable bond, or groups that can be selectively converted to such reactive functions,
C is a selectively cleavable group,
m is an integer from 1 to 20,
n is an integer from 0 to 20, and
p is 0 or 1,
adjacent to the immobilized oligonucleotide prepared in step (i).

15. The method according to claim 1, wherein the immobilized oligonucleotide prepared in step (i) comprises a structure of the general formula:

and wherein the solid support exhibits a structure of the general formula:

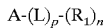

wherein:
A is a support-anchoring group,
L is a linker,
R₁ and R are reactive functions capable of reacting with each other to form a stable bond, or groups that can be selectively converted to such reactive functions,
C is a electively cleavable group,
m is an integer from 1 to 20,
n is an integer from 0 to 20, and
p is 0 or 1,
adjacent to the immobilized oligonucleotide prepared in step (i).

16. The method according to claim 11, wherein the immobilized oligonucleotide prepared in step (i) comprises a structure of the general formula:

and wherein the solid support exhibits a structure of the general formula:

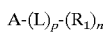

wherein:
A is a support-anchoring group,
L is a linker,
R₁ and R are reactive functions capable of reacting with each other to form a stable bond, or groups that can be selectively converted to such reactive functions,
C is a selectively cleavable group,
m is an integer from 1 to 20,
n is an integer from 0 to 20, and
p is 0 or 1,
adjacent to the immobilized oligonucleotide prepared in step (i).

17. The method according to claim 16, wherein one of R and R₁ is an electrophilic group and the other is a nucleophilic group.

18. The method according to claim 17, wherein the nucleophilic group is selected from hydroxyl, amine thiol, hydrazide, hydrazine, semicarbazide, carbohydrazide and hydroxylamine groups.

19. The method according to claim 16, wherein the electrophilic group is selected from activated carboxyl, activated phoshonomonoester, activated H-phosphonate, activated phosphodiester, formyl, keto, activated disulfide, maleimide and activated halogen.

20. The method according to claim 19, wherein the nucleophilic group is hydroxyl and the electrophilic group is X-B, where X is phosphodiester and B is a group removable from a phosphotriester to form a phosphodiest r, such as 2-chlorophenyl, 2,4-dichlorophenyl, 2-nitrophenyl, 4-nitrophenyl, 4-nitrophenylethyl and 2-cyanoethyl.

21. The method according to claim 16, wherein the group C is selected from a tetra-substituted disiloxyl group, a di-substituted siloxyl group, a group removable by redox conditions, a group removable by metal-ion catalysis, a cis-diol group protected at one hydroxy by any one of the foregoing groups, and a phosphoramide group or an ester group.

22. The method according to claim 16, wherein the anchoring group A is selected from amide, phosphoramide, phosphodiester, phosphotriester, and ether groups.

23. The method according to claim 16, wherein die linker L is branched and comprises at least two starting points for oligonucleotide synthesis.

24. The method according to claims 16, wherein the solid support is selected from optionally cross-linked polystyrenes, polypropylene, polyethylene, polytetrafluoroethylene, optionally cross-linked polysaccharides, silica, and glasses.

25. A method for preparing an immobilized oligonucleotide having a free 3'-end comprising the steps of:
(i) providing an oligonucleotide attached at its 3' end, to a solid support via a solid support-anchoring group and having a free 5'-end, wherein said oligonucleotide has a structure of the general formula:

wherein:
A is a solid support-anchoring group,
L is a linker,
R is a first reactive function capable of reacting with a second reactive function to form a stable bond,
R₁ is a group that can be selectively converted to a second reactive function,
C is a selectively cleavable group,
m is an integer from 1 to 20,
n is an integer from 1 to 20, and
p is 0 or 1;
(ii) Covalently coupling a group to said R₁ group thereby converting said R₁ group into a second reactive function;
(iii) Reacting said first reactive function with said second reactive function to form a stable bond; and
(iv) Selectively cleaving said C group.

26. The method of claim 25 wherein n is equal or greater than 2 and equal or less than 10.

27. The method of claim 25 wherein n is equal or greater than 2 and equal or less than 10 and said R₁ group is in a branched form.

28. The method of claim 25 wherein m is equal or greater than 2 and equal or less than 10.

29. The method of claim 25 wherein said second reactive function is amine.

30. The method of claim 25 wherein said R group is carboxyl.

31. The method of claim 25 wherein said R₁ group is hydroxyl.

32. A method for preparing an immobilized oligonucleotide having a free 3'-end comprising the steps of:
(i) providing an oligonucleotide attached at its 3' end to a solid support via a solid support-anchoring group and having a free 5'-end, wherein said oligonucleotide has a structure of the general formula:

wherein:
A is a solid support-anchoring group,
L is a linker,
R is a first reactive function capable of reacting with a second reactive function to form a stable bond or a group that can be selectively converted to a first reactive function, $R_1$ is a second reactive function capable of reacting with a first reactive function to form a stable bond or a group that can be selectively converted to a second reactive function, C is a selectively cleavable group, m is an integer from 1 to 20, n is an integer from 2 to 20, and p is 0 or 1;

(ii) Reacting said first reactive function with said second reactive function to form a stable bond; and (iii) Selectively cleaving said C group.

* * * * *

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence -continued

```
<220> FEATURE:
<223> OTHER INFORMATION: synthetic oligonucleotide template of M13-30
      complementary to the synthesized sequence

<400> SEQUENCE: 1
gtcgacctgc aggcatgcaa gcttggcact                                     30
```